US007713581B2

(12) United States Patent
Heidlas et al.

(10) Patent No.: US 7,713,581 B2
(45) Date of Patent: May 11, 2010

(54) METHOD OF IMPREGNATING A CARRIER A MATRIX WITH SOLID AND/OR LIQUID COMPOUNDS USING COMPRESSED GASES, AND MATERIALS THUS IMPREGNATED

(75) Inventors: Jürgen Heidlas, Trostberg (DE); Zhengfeng Zhang, Trostberg (DE); Kurt Stork, Abensberg (DE); Johann Wiesmüller, Garching (DE); Martin Ober, Altenmarkt (DE); Johann Obersteiner, Feichten (DE)

(73) Assignee: Degussa AG, Dusseldorf (DE)

( * ) Notice: Subject to any disclaimer, the term of this patent is extended or adjusted under 35 U.S.C. 154(b) by 0 days.

(21) Appl. No.: 11/598,484

(22) Filed: Nov. 9, 2006

(65) Prior Publication Data

US 2007/0054032 A1  Mar. 8, 2007

Related U.S. Application Data

(63) Continuation of application No. 10/362,136, filed as application No. PCT/EP01/09669 on Aug. 21, 2001, now abandoned.

(30) Foreign Application Priority Data

Aug. 22, 2000   (DE)   ................. 100 41 003

(51) Int. Cl.
  *B05D 7/00*   (2006.01)
  *B05D 3/04*   (2006.01)
  *B01J 13/02*  (2006.01)
  *A61J 3/07*   (2006.01)
(52) U.S. Cl. .............. 427/212; 427/2.1; 427/213.3; 427/213.31; 264/4; 264/4.32
(58) Field of Classification Search ............... None
  See application file for complete search history.

(56) References Cited

U.S. PATENT DOCUMENTS

| 4,737,384 A | * | 4/1988 | Murthy et al. | .............. 427/369 |
| 5,271,881 A | * | 12/1993 | Redding, Jr. | ............... 264/4.32 |
| 5,766,637 A | * | 6/1998 | Shine et al. | ................. 424/497 |

* cited by examiner

*Primary Examiner*—Timothy H Meeks
*Assistant Examiner*—Cachet I Sellman
(74) *Attorney, Agent, or Firm*—Fulbright & Jaworski LLP

(57) ABSTRACT

The invention relates to a method for impregnating a support matrix with solid and/or liquid compounds using a compressed gas or a compressed mixture of gases at densities ranging from 0.15 to 1.3 kg/l and at least two unsymmetrical pressure changes (pulsations). The method is further characterized in that both a multitude of impregnating substances such as biologically active compounds, technical materials or metal-organic compounds, as well as support matrices of biological origin and organic or inorganic substances can be used that have large inner surfaces and/or inner surfaces that are difficult to access.

25 Claims, No Drawings

METHOD OF IMPREGNATING A CARRIER A MATRIX WITH SOLID AND/OR LIQUID COMPOUNDS USING COMPRESSED GASES, AND MATERIALS THUS IMPREGNATED

This application is a continuation application of U.S. Ser. No. 10/362,136 filed May 29, 2003 now Abandoned, incorporated herein by reference in its entirety, which is a §371 of ÿ PCT/EP01/09669 filed Aug. 21, 2001, which claims priority from German 100 41 003.0 filed Aug. 22, 2000.

The present invention relates to a method of impregnating a carrier matrix with solid and/or liquid compounds using compressed gases or gas mixtures, and materials impregnated in this manner.

In the last 20 years, the use of compressed gases as solvent has developed markedly in industry. After the extraction of natural substances, for example methods of decaffeination, principally played a role in the 1980s, the potential use of compressed gases has shifted in the 1990s to the "material sciences": supercritical gases are thus now being used, inter alia, in chemical processes for reducing the viscosity of solutions or for producing ultrafine particles. In the very near future, it is expected that supercritical gases will increasingly be used in chemical process engineering.

Because of its inert properties, its toxicological safety, availability and physical and physicochemical properties, carbon dioxide plays the most important role concerning supercritical solvents in process engineering in general (McHugh & Krukonis, *Supercritical Fluid Extraction*, 2nd Edition, Butterworth-Heinemann, Boston, 1994).

An important motivation for using gases in the supercritical state is frequently their markedly lower viscosity compared with "liquid" solvents and the fact that the density in the supercritical state can be continuously controlled within a wide range by varying the process pressure. Since the density of the supercritical gas, in a simplified consideration, correlates with its dissolving power, this gives the ideal prerequirements for carrying out selective extractions or separations. In the prior art, many processing examples are described in which the selectivity of extraction, in particular in the case of natural substances plays a critical role, which justifies the use of supercritical gases from economic aspects (Stahl et al., *Verdichtete Gase zur Extraktion und Raffination* [compressed gases for extraction and refining], Springer, Heidelberg, 1987).

On account of the abovementioned properties, gases in the compressed state, however, can be used not only for selective extraction of substances, that is to say for separations, but also for impregnation, that is to say depositing what are termed "impregnation materials" onto a carrier matrix. Here, again, the very high diffusivity, owing to their low viscosity, of the supercritical gases, that is to say their ability to penetrate very readily into a "compact" and only poorly accessible matrix, plays an important role. An impregnation material can be deposited in a targeted manner in the carrier matrix via targeted control of the solution properties.

In the prior art, for example, according to German patent DE 21 27 642, aroma substances are first extracted from tea and collected, the caffeine is thereupon removed from the tea and then the aroma substances are restored to the decaffeinated tea ("restoration by impregnation"). The aroma substances are extracted here using dry carbon dioxide, while the caffeine is extracted using water as entrainer. Applying the aroma substances to the tea matrix is simple in processing terms, since the aroma substance fraction has a very high solubility in the carbon dioxide and the tea matrix is readily accessible. In addition, it is of no importance how "deep" the aroma substances penetrate into the matrix, since a fairly uniform distribution on the individual particles of the tea is sufficient.

There are, in the prior art, as described by the example above, methods using supercritical gases in which impregnation materials are deposited on a carrier matrix and, assuming an appropriate solubility of the impregnation material in the gas and relatively easy accessibility of the carrier matrix, can also be introduced into a carrier matrix. However, if the solubility of the impregnation materials in the gas is low and the accessibility of the carrier matrix is restricted, for example due to adverse distribution coefficients of the impregnation materials between gas and carrier matrix, no satisfactory methods are available for being able to introduce the impregnation materials into the carrier matrix economically. Low solubility is taken to mean, in particular, if 30 to 100 parts (sparingly soluble), 100-1000 parts (slightly soluble) or 1000 or more parts, in particular up to 10,000 parts (very slightly soluble) of the solvent are required to dissolve 1 part of impregnation material.

An object of the present invention was thus to develop a method for impregnating a carrier matrix with solid and/or liquid compounds using compressed gases, in which the impregnation materials can be transported efficiently from the surface into the interior of the respective carrier matrix, in which case an application spectrum as broad as possible is to be covered.

This object was achieved according to the invention by the means that the solid and/or liquid compound(s) (impregnation material) and the insoluble carrier matrix are brought into contact with a compressed gas (mixture) at gas densities of at least 0.15 to 1.3 kg/l under at least 2, preferably at least 3, more preferably at least 5, and particularly preferably at least 10, unsymmetrical pressure change cycles (pulsations) in such a manner that, per individual pulsation of a period of at least 5 s to 60 min, preferably from at least 50 s to 20 min, particularly preferably of at least 100 s to 10 min, the respective time period to achieve the pressure maximum is greater than the time period of the pressure reduction to the minimum.

This method thus exploits the differing solubility of the impregnation materials at different densities of the compressed gases in the near-critical region, in order to transport the impregnation material actively from the exterior into the interior of the carrier matrix. The near-critical region is generally defined by a reduced temperature of a compressed gas in the range from 0.9 to 1.5 and a reduced pressure in the range from 0.8 to 5, these said differential quantities each being the ratios of the working temperature and the working pressure to the critical temperature and the critical pressure, respectively.

Surprisingly, by means of the inventive method and in particular the pulsations, it is possible to utilise kinetic dissolution effects in order to achieve active material transport of the impregnation materials into the carrier matrix from the exterior into the interior: when the pressure is increased in the supercritical state, the density of the gas increases and thus also its dissolving power for the impregnation materials. Starting from a low gas density and proceeding towards a higher density, this leads to an influx of the gas into the carrier matrix, with the high diffusivity of the gas system in the supercritical state being a particular advantage. In addition, it has been found that, on account of the increasing gas density, the impregnation materials simultaneously are dissolved better in the gas and together with the influx of the gas are transported into the matrix. If adsorption and mass partition effects in the matrix are then excluded, when the gas density is reduced, that is a pressure reduction, the impregnation material would exit again from the matrix together with the gas efflux. However, surprisingly, this is essentially avoided by the time period for pressure reduction being shorter than the time period for pressure increase. This is because during a short expansion time, the desired material irreversibly precipitates out in the matrix, while during the preceding slower pressure increase, sufficient time remains for the impregnation materials to dissolve in the gas (mixture) and be transported with it into the matrix. These effects could not be predicted in this clarity.

The number of pressure pulsations, the time of the pulsation cycles and the pressure and density differences, respectively, generally depend on the impregnation material, the carrier matrix which is to be impregnated, the plant-specific preconditions, and the targeted extent to which the desired impregnation materials are to be distributed into/in the matrix.

Inter alia, it is to be considered as essential to the invention that the time period to achieve the respective peak maximum ($t_{to\ max}$) per pulsation is greater than the time period for the pressure reduction to the peak minimum ($t_{to\ min}$): $t_{to\ max} > t_{to\ min}$. Depending on the size of the production plant, the duration of an individual pulsation is at least 5 s to 60 min, preferably at least 50 s to 20 min, particularly preferably at least 100 s to 10 min. It has proved to be expedient in terms of the process, if $t_{to\ max} \gg t_{to\ min}$, where $t_{to\ max}$ is in particular 5 to 30 times, preferably 9 to 25 times, greater than $t_{to\ min}$ since then back-transport of the impregnation materials from the carrier matrix can be most effectively suppressed. However, the minimum time period for pressure and density reduction, respectively, can also be limited by the fact that the carrier matrix becomes "unstable", that is to say is damaged, by the rapid density change, and, in particular, formally "collapses". However, the course of the process can be set empirically in such a manner that this damage to the matrix can be excluded.

The present method can be used for producing a multiplicity of products and intermediates in which impregnation materials are introduced into a carrier matrix. Suitable representatives of impregnation materials have proved to be all biologically active compounds, such as pharmaceutical, agrochemical and cosmetic active compounds, technical substances, for example surface-active or surface-modifying compositions (hydrophobization or hydrophilization) or organometallic compounds. Compounds which are used in this context are, in particular, vitamins, nutraceuticals, plant-treatment compositions, insecticides, fungicides, herbicides (that is to say biocides in general), phytohormones, for example cytokinins, but also aroma substances, pigments and other impregnation materials which have another functionality, such as dispersants, emulsifiers or chemically reactive compounds, for example surface-reactive compounds. It is thus also possible in the context of the present invention that, after introducing the impregnation materials into the carrier matrix, a chemical reaction is induced in-situ in the process, for example by a temperature increase or feeding in reaction initiators, in order to achieve chemical bonding of the impregnation material on the carrier matrix.

The sole precondition for suitability as an impregnation material is its ability to dissolve in the compressed gas (mixture).

Preferred representatives of carrier matrices are all materials of biological origin, for example foods, feeds, seed material, and other organic and inorganic carrier matrices which preferably have large and/or poorly accessible internal surface areas. This also includes carrier matrices which increase their volume under the process conditions, which is generally achieved by swelling, and as a result of which the external surface areas and also their internal surface areas increase.

In particular, compounds which are suitable are according to the invention synthetic, semi-synthetic and natural organic polymers, for example polyethylenes (PE), polypropylenes (PP) or polyglycolic acids (for example polylactic-glycolic acid, PLGA) or carbohydrates, for example starches and cyclodextrins, in addition inorganic carrier materials, in particular those having large internal surface areas, for example silicon dioxides, such as precipitated or pyrogenic silicic acids or silica gels, alumosilicates or other catalyst base materials, for example zeolites, and aluminium oxides, activated carbons, titanium dioxides, bentonites, which can all be used in chemically or physically modified form. The carrier matrices having an open or closed pore internal structure can be (pre)swollen, or can be extruded or foamed matrices.

In practice, in the present method, a very large density range of the compressed, that is to say near-critical or super-critical, gases or gas mixtures can be utilised; it is in the limits essential to the invention of at least 0.15 to 1.3 kg/l, preferably from at least 0.4 to 1.0 kg/l, and particularly preferably from at least 0.5 to 0.9 kg/l. In order to be able to establish these densities by process engineering, the process pressures according to the invention vary from at least 5 to 800 bar, with pressure ranges from at least 30, in particular at least 50 to 500 bar, being preferred. The process temperature should preferably be above the critical temperature of the gas or gas mixture used, in particular at least 31° C. to 200° C., preferably at least 40° C. to 150° C., particularly preferably at least 50° C. to 100° C.

The choice of suitable gas or suitable gas mixtures also depends essentially on the impregnation material or the mixture of different impregnation materials which are being introduced into the carrier matrix. Fundamentally, therefore, gases/gas mixtures come into consideration whose critical state parameters are within industrially practicable limits. Inter alia the critical temperature of the gas system is particularly important, which, at excessive values, may cause thermal damage to both the impregnation materials and also the carrier matrix. Suitable gases for the present method have thus proved to be carbon dioxide, propane, butane, ethane, ethylene, dimethyl ether, ammonia, halogenated hydrocarbons, comprising fluorinated, chlorinated, brominated and iodated branched or unbranched hydrocarbons from $C_1$ to $C_4$, in particular partially or completely fluorinated hydrocarbons, or their mixtures.

A precondition for being able to carry out the method of the invention is that the impregnation materials, in the pressure peak maximum, have partly a substantially higher solubility in the gas (mixture) than in the pressure trough minimum. In contrast, the impregnation matrix, that is to say the carrier matrix, under the given processing conditions, must be insoluble both in the near-critical and also in the supercritical state of the gas (mixture). The absolute pressure minimum is set in this case by the minimum dissolving power of the gas (mixture) for the impregnation material and the absolute pressure maximum is set by the maximum solubility of the impregnation materials in the compressed gas (mixture).

The pressure range from the absolute pressure minimum to the absolute pressure maximum is the range in which operations can take place in principle, but which need not be exploited completely.

Preferably, the pressure in the pressure maximum of a pulse is 1.1 times, more preferably 1.3 times, still more preferably 1.5 times, still more preferably twice, most preferably 5 times, the pressure at the pressure minimum. In addition, it is preferred to set the pressure in the pressure maximum in such a manner that it is at least 1 bar, preferably at least 5 bar, more preferably at least 10 bar, and most preferably at least 20 bar, higher than the pressure in the pressure minimum. In this case the dissolving power of the gas (mixture) in the pressure maximum is preferably at least twice, preferably at least 10 times, better than the dissolving power of the gas (mixture) in the pressure minimum.

In order to achieve the most effective mass transport of the impregnation materials from the surface into the interior of the carrier matrix, the density difference during the individual pulsation should be as large as possible. The most expedient practical lower limit of the density minimum then occurs when the gases or the gas mixtures no longer have any dissolving power for the impregnation materials. With respect to density, there is, for the method, in principle, no upper limit in the peak maximum. However, since the method is based on the principle of transport of the gas influx or gas efflux in the carrier matrix at different densities, it is in practice no longer expedient, and also generally uneconomic, to use more than 10 times the supercritical pressure of the corresponding gas or gas mixture, since the density then experiences markedly lower changes than in the near-critical state range of the gas system.

With respect to the individual pulsations which always consist of the sum of the two time periods for pressure increase and pressure reduction, the invention envisages that their periods can differ from one another. That is to say the period of an individual pulsation can be shorter or also longer than the preceding and/or subsequent pulsation, an individual pulsation lasting from at least 5 s to 60 min, preferably from at least 50 s to 20 min, particularly preferably from at least 100 s to 10 min.

However, in certain method variants, it can also be necessary that the respective time periods within different individual pulsation periods differ from one another, which means nothing other than that the time periods for the pressure increase and/or the time periods for the pressure reduction differ from one another from individual pulsation to individual pulsation. However, it is important that even in these cases, per individual pulsation, the time period for the pressure increase is always greater than the time period for the pressure reduction. It is also possible to choose the pressure minima and/or pressure maxima differently in the individual pulses.

However, liquid aids that improve in particular the solubility of the impregnation materials, can also be added to the near-critical gas or to the gas mixtures, particularly preferably at atmospheric pressure. Such suitable aids are, for example, water or organic solvents selected from the group consisting of short-chain alcohols, ketones and esters, branched or unbranched, having chain lengths from $C_1$ to $C_{10}$, preferably $C_1$ to $C_8$, particularly preferably from $C_2$ to $C_3$, and/or having surface activity, which can be used, typically, in concentrations up to 20% by weight, preferably from 1% by weight to 10% by weight, particularly preferably from 2% by weight to 5% by weight. However, in principle, entrainers can also be used, which, for example, set a suitable pH environment in the process gas. Those which are suitable, in particular, for this are organic amines, for example triethylamine or ammonia, which can additionally improve the solubility of the impregnation materials.

In this case the aids and/or entrainers which are mentioned as preferred, but also all other suitable aids and/or entrainers, can also be added to the impregnation material, which again should preferably be performed at atmospheric pressure. Other substances which can be used not only as actual impregnation materials, but also as aids, are surface-active substances, since they themselves have good solubility in the supercritical gas (mixture) (what are termed "gasophilic surfactants"). Using the surfactants not only improves the solubility of certain impregnation materials in the gas (mixture), the surfactants acting in this case as aid, they also facilitate the penetration of the impregnation materials into the carrier matrix, since the diffusivity of the mass system impregnation materials/gas (mixture) is increased by a further reduction in surface tension. However, if the "gasophilic surfactants" are used as actual impregnation materials, the purpose of the impregnation process can be modification of the surface properties of the carrier matrix, for example the improvement or reduction of their water-wettability and the associated properties.

Regarding the embodiment of the method in the context of the present invention, various variants are possible, since the inventive method is limited generally to the transport of the impregnation materials into the carrier matrix, and does not claim the manner in which the impregnation materials are to be deposited on the surface of the carrier matrix.

Typically, the method is carried out in an autoclave, and preferably in a discontinous batch process.

In a special variant, a preliminary stage is provided for the inventive method, in which preliminary stage, after the autoclave is filled with the carrier matrix and the impregnation materials, the plant system is brought, by the suitable gas (mixture), to the corresponding pressure at which the impregnation materials exhibit the above described solubility behaviour. The gas or the gas mixture is then, in the supercritical state, circulated in such a manner that the impregnation materials are distributed on the carrier matrix and the concentration gradient of the active compounds in the bed of the carrier matrix achieves an acceptable minimum value. The process pressure, and thus the density of the gas system, is then reduced in such a manner that the impregnation materials settle (precipitate; are deposited) on the surfaces of the carrier matrix. Although, in this procedure, owing to the good diffusivity of the gas (mixtures) in the supercritical state, some of the active compounds can already penetrate into the interior of the carrier matrix, but a significant proportion always remains on the surface of the carrier matrix, since this proportion of impregnation material separates there from the gas phase of the intergranular volume. Then, as described above, the actual pulsation that is essential to the invention is carried out, in order to achieve transport from the exterior to the interior of the carrier matrix.

From practical, and especially economic, aspects, an alternative procedure can also be suitable, especially if the solubility of the impregnation materials, even in the supercritical state of the gas (mixture), is only low, and a long process time is required for recirculating the gas or the gas mixture in the autoclave, to achieve the desired distribution in the carrier matrix packed bed, that is to say to minimise its concentration gradient in the packed bed. For these cases, the invention provides precoating the carrier matrix with the impregnating materials by means of conventional technology, such as, in particular, the known methods for spray coating, in particular in the fluidized bed, or else melt coating. In this case the impregnating materials are applied to the wall of the carrier matrix particles, without the impregnating materials being able to penetrate, at any rate essentially, into the internal region of the matrix particles. The material thus prepared is then also subjected to the pulsation process essential to the invention for impregnation, as a result of which the impregnation materials are only then transported into the interior of the carrier matrix. This procedure can have enormous economic advantages, since the actual transport path which must be overcome by the impregnating material that is dissolved in the gas (mixture) is very short, that is to say only from the surface of the matrix particles into their interior. In addition, via this procedure, the individual loading of the matrix particles with impregnating material can be controlled and ensured markedly better.

The present method thus has great potential, especially, for introducing pharmaceutical active compounds into a suitable carrier matrix having a large internal surface area, as required in the production of preparations having delayed release of active compound.

A further application example is impregnating or disinfecting seed material, the critical advantage of the inventive process being that the plant treatment composition does not, as hitherto in the prior art, remain solely in the outer regions of the seed grain, but can be introduced into the internal region of the seed body. For certain applications, this can lead to an improved effect with simultaneously lower dosages.

Finally, the impregnating materials used can also be organometallic substances which are to be introduced into a matrix, as is customary in particular in the production of supported catalysts.

In addition to the inventive method with its preferred variants, the present invention also relates to all impregnated substances produced using this method.

The examples below are intended to illustrate the advantages of the inventive method and the substances produced therewith.

EXAMPLES

Example 1

Impregnation of a Compact Plant Material (Rice Grains) with Lipophilic Impregnating Materials (β-Carotene as Marker Substance)

1.1 Unsymmetrical Pulsation Cycles (Invention):

100 ml of a vegetable oil which contained approximately 3% by weight of β-carotene (impregnation material) was sprayed, using a fine nozzle, onto 2 kg of commercial husked rice grains as carrier matrix (bulk density approximately 0.6 kg/l) at room temperature in an agitating drum, while the drum charge was mixed thoroughly for approximately 30 minutes. This achieved a uniform application of the coloured oil onto the surface of the rice grains. Study of the cross section of a single grain by light microscopy showed that only the edge region of the cross-sectional area had red staining due to the pigment. The starting material thus pretreated was then introduced into an insert vessel (volume 3.5 l) that was closed at the top and bottom with metal sinter plates. The insert vessel which was completely filled with rice grains was inserted into the pressure autoclave of a high-pressure extraction system. The autoclave was first brought at 50° C. (set by means of jacket heating) to a pressure of 150 bar (pressure minimum) with carbon dioxide. The pressure was then slowly increased to 500 bar over a period of 5 min using a high-pressure pump (pressure maximum) and then rapidly reduced back to 100 bar in the course of 15 s via a pressure control valve. This pulsation operation was repeated in the same manner 20 times. After expanding the system to atmospheric pressure, the rice grains were taken out and the result of impregnation was compared with the starting material. The red-stained pigment zone had disappeared from the edge regions and in the light microscope, an even staining of the starch body over the entire cross section of the rice grain with β-carotene was observed.

1.2 Symmetrical Pulsation Cycles (Comparison):

Rice grains were pretreated in a similar manner to Example 1.1, the actual impregnation being carried out symmetrically in the same pressure range with 20 pulsations, that is to say the time for the pressure rise to the maximum was identical to the time for pressure reduction to the minimum, that is to say in each case 2.5 min.

Study by light microscopy of the cross section of a rice grain thus treated showed only an unclear and washed out pigment zone in the edge region, but the pigment β-carotene was not distributed over the entire cross-sectional area of the grain.

Example 2

Impregnation of a Porous Inorganic Carrier Matrix (Endobon®) with a Pharmaceutical Active Compound (Ketoprofen)

5 g of ketoprofen were dissolved in 150 ml of methanol and the solution, together with 15 g of Endobon® (Merck; porous hydroxyapatite granules, Ø 2.8 to 5.6 mm), was transferred to a round-bottomed flask. The solvent was removed under reduced pressure on a rotary evaporator with agitation.

The starting material thus pretreated was introduced into an insert vessel (volume 0.5 l) which was sealed at the top and bottom with metal sinter plates. The insert vessel was inserted into the pressure autoclave of a high-pressure extraction system. The autoclave was first, at 50° C. (set using jacket heating), brought to a pressure of 100 bar (pressure minimum) with carbon dioxide which contained 1% by weight of methanol as entrainer. The pressure was then slowly increased to 250 bar (pressure maximum) over a period of 3 min, using a high-pressure pump, and then rapidly reduced to 100 bar via a pressure control valve in the course of 20 s. This pulsation operation was repeated 10 times in the same manner. After expanding the system to atmospheric pressure, the impregnated carrier matrix was removed.

For characterization, the release rate of ketoprofen on the carrier matrix was determined in a dissolution test and compared with a starting material that had not been subjected to the pulsation impregnation, and with a sample which had been treated with symmetrical pulsation cycles (1.5 min in each case for pressure rise and decrease). The sample from Example 2 (invention) showed the longest release curve, followed by the symmetrically treated pulsation material (comparison); the shortest release curve was shown by the pre-coated starting material that had not been subjected to a pressure treatment.

The experimental result makes clear, by the example of ketoprofen, that release is slowest (sustained release) from the internal surfaces, and that using the inventive process the active transport into the internal surface of the carrier matrix can be carried out most effectively.

Example 3

Impregnation of a Porous Organic Carrier Polymer (Accurel®) with a Silicone Oil 20 g of Accurel® granules (Akzo; high-porosity polypropylene) were introduced into an insert vessel (volume 0.5 l) which was closed at the top and bottom with metal sinter plates. The insert vessel was inserted into the pressure autoclave of the high-pressure extraction system. The autoclave was first, at 96° C. (set by means of jacket heating), brought to a pressure of 100 bar with propane. 10 g of silicone oil (dimethylpolysiloxane having a viscosity of 10,000 mPas) were then pumped in upstream of the autoclave and recirculated together with 1 kg of propane isothermically and isobarically, in order to achieve uniform distribution of the silicone oil in the packed bed of the Accurel carrier matrix. The pressure was then reduced to 43 bar, which decreased the solubility of the silicone oil in the propane.

In 8 pulsation cycles the pressure was then increased from 43 bar (pressure minimum) to 70 bar (pressure maximum) (time for pressure rise: 2 min) and decreased (time for pressure drop: 5 s). The system was then brought to atmospheric pressure and the result of impregnation was evaluated.

In contrast to Accurel samples that had been removed from the autoclave before the inventive pulsation and on which surfaces silicone oil was clearly adherent, the silicone oil in the samples impregnated according to Example 3 had virtually completely disappeared from the surface of the polypropylene matrix and migrated into the interior of the polymeric carrier. The result was markedly worse when, for comparison, symmetrical pulsation cycles were carried out in a similar pressure range (1 min in each case for the pressure rise and drop).

The invention thus relates in particular to a method of impregnating a carrier matrix with solid and/or liquid compounds using compressed gases which is essentially characterized in that the solid and/or liquid compound(s) (impregnating material) and the insoluble carrier matrix are brought into contact with a compressed gas (mixture) at gas densities between 0.15 and 1.3 kg/l under at least two unsymmetrically preceding pressure-change cycles (pulsations) in such a manner that, per individual pulsation of a duration between 5 s and 60 min, the respective time period to achieve the pressure maximum is greater than the time period for pressure reduction to the minimum, the absolute pressure minimum being established by the minimum dissolving power of the gas (mixture) for the impregnating material and the absolute pressure maximum being established by the maximum solubility of the impregnating materials in the compressed gas (mixture). The method is distinguished in that not only a multiplicity of impregnation materials, for example biologically active compounds, industrial substances or organometallic compounds, can be used but also carrier matrices of biological origin and organic or inorganic substances, which all have large and/or poorly accessible internal surface areas. By means of this method, which is preferably carried out using compressed carbon dioxide, propane, butane, ethane or ammonia, not only can untreated carrier material be handled but also already precoated material. As a result, impregnated materials are obtained whose internal surfaces are substantially homogeneously coated with the impregnation materials and which can be used, especially, in the pharmaceutical, agrochemical, cosmetic and technical sectors.

The invention claimed is:

1. A method of impregnating a carrier matrix with at least one impregnating material comprising at least one solid or liquid compound using compressed gas, said compressed gas having a critical temperature and a critical pressure, comprising:

contacting said at least one impregnating material and said carrier matrix with a compressed gas at a gas density of from 0.15 to 1.3 kg/l under at least two unsymmetrical pressure pulsations in such a manner that, per individual pulsation of a duration of from 5 s to 60 min, the respective time period to achieve the pressure maximum is greater than the time period for pressure reduction to the pressure minimum, wherein said carrier matrix is not soluble in said compressed gas and wherein the solubility of said impregnating material in said compressed gas is higher in the pressure maximum than in the pressure minimum, wherein the time period to achieve the pressure maximum is from 5 to 30 times greater than the time period for pressure reduction to the pressure minimum.

2. The method of claim 1, wherein said compressed gas is selected from the group consisting of carbon dioxide, propane, butane, ethane, ethylene, dimethyl ether, ammonia, halogenated $C_1$-$C_4$ hydrocarbons and mixtures thereof.

3. The method of claim 1, wherein said carrier matrix is of biological origin.

4. The method of claim 3, wherein said carrier matrix is a food, a feed or a seed material.

5. The method of claim 1, wherein said carrier matrix is a synthetic, semisynthetic or natural organic polymer.

6. The method of claim 5, wherein said carrier matrix is a polyethylene, a polypropylene, a polyglycolic acid or a carbohydrate.

7. The method of claim 1, wherein said carrier matrix is selected from the group consisting of silicon dioxide, alumosilicates, zeolites, aluminum oxide, activated carbon, titanium dioxide and bentonite.

8. The method of claim 1 wherein said carrier matrix is precipitated silica, pyrogenic silica or silica gel.

9. The method of claim 1 wherein said impregnating material is a biologically active compound, a technical substance or an organometallic compound.

10. The method of claim 9, wherein said biologically active compound is a pharmaceutical, an agrochemical or a cosmetic active compound.

11. The method of claim 9, wherein said biologically active compound is a vitamin, a nutraceutical, a plant-treatment agent, a biocide or a phytohonnone.

12. The method of claim 1 wherein said impregnating material is an aroma substance, a pigment, a dispersant, an emulsifier, a surface active-compound or a surface-reactive compound.

13. The method of claim 1, wherein an aid for changing the solubility or having surface activity is added to the gas.

14. The method of claim 13, wherein said aid is water or an organic solvent selected from the group consisting of short-chain alcohols, ketones and esters.

15. The method of claim 13, wherein said aid is added in a concentration of up to 20% by weight.

16. The method of claim 1, wherein an entrainer for setting pH is added to the gas.

17. The method of claim 1, wherein an entrainer is ammonia or an organic amine.

18. The method of claim 1, wherein said contacting is carried out in an autoclave in a discontinuous batch process.

19. The method of claim 1, wherein the components, before the pulsation, are brought to the process pressure to which the impregnating materials exhibit their optimum solubility behavior, then the gas is recirculated in the supercritical range in such a manner that the impregnating materials are distributed on the carrier material and then the process pressure is reduced in such a manner that the impregnating materials settle on the surfaces of the carrier material.

20. The method of claim 1, wherein said carrier matrix is precoated with said impregnating material.

21. The method of claim 1, wherein said carrier matrix is not soluble in said compressed gas and wherein the solubility of said impregnating material in said compressed gas is higher in the pressure maximum than in the pressure minimum, wherein said compressed gas is at a reduced temperature of from 0.9 to 1.5 and a reduced pressure of from 0.8 to 5, the reduced temperature being the ratio of the temperature to the critical temperature of said compressed gas and the reduced pressure being the ratio of the pressure to the critical pressure of said compressed gas.

22. The method of claim 1, wherein said compressed gas is at a temperature above the critical temperature of said compressed gas.

23. The method of claim 1, wherein said gas density is from 0.4 to 1.0 kg/l.

24. The method of claim 1, wherein the durations of the individual pulsations differ from one another.

25. The method of claim 1, wherein the time periods for at least one of the pressure increase or for the pressure reduction of the individual pulsations differ among one another from one another.

* * * * *